US009778232B2

(12) United States Patent
Yotani et al.

(10) Patent No.: US 9,778,232 B2
(45) Date of Patent: Oct. 3, 2017

(54) COLUMN DEVICE FOR LIQUID CHROMATOGRAPHY AND LIQUID CHROMATOGRAPHY APPARATUS

(71) Applicant: Sekisui Medical Co., Ltd., Tokyo (JP)

(72) Inventors: Takuya Yotani, Tokyo (JP); Takayuki Oka, Tokyo (JP); Hideki Muraki, Tokyo (JP)

(73) Assignee: Sekisui Medical Co., Ltd. (JP)

( * ) Notice: Subject to any disclaimer, the term of this patent is extended or adjusted under 35 U.S.C. 154(b) by 68 days.

(21) Appl. No.: 14/775,402

(22) PCT Filed: Mar. 11, 2014

(86) PCT No.: PCT/JP2014/056260
§ 371 (c)(1),
(2) Date: Dec. 14, 2015

(87) PCT Pub. No.: WO2014/142096
PCT Pub. Date: Sep. 18, 2014

(65) Prior Publication Data
US 2016/0103103 A1 Apr. 14, 2016

(30) Foreign Application Priority Data
Mar. 11, 2013 (JP) .................................. 2013-047880

(51) Int. Cl.
| | | |
|---|---|---|
| G01N 30/60 | (2006.01) | |
| G01N 30/16 | (2006.01) | |
| G01N 30/88 | (2006.01) | |

(52) U.S. Cl.
CPC ......... *G01N 30/6026* (2013.01); *G01N 30/16* (2013.01); *G01N 30/603* (2013.01);
(Continued)

(58) Field of Classification Search
CPC .......... G01N 30/6026; G01N 30/6047; G01N 30/6004; G01N 30/6052; G01N 30/606
See application file for complete search history.

(56) References Cited

U.S. PATENT DOCUMENTS

| 4,476,017 A | 10/1984 | Scharff et al. |
|---|---|---|
| 4,670,141 A * | 6/1987 | Shackelford ........... G01N 30/52 |
| | | 210/198.2 |
| 2005/0247632 A1 | 11/2005 | Ellis et al. |

FOREIGN PATENT DOCUMENTS

| JP | S50-150497 A | 12/1975 |
|---|---|---|
| JP | S59-210363 A | 11/1984 |
| | (Continued) | |

OTHER PUBLICATIONS

International Search Report from International Publication No. PCT/JP2014/056260 mailed Apr. 28, 2014.
(Continued)

*Primary Examiner* — Paul West
(74) *Attorney, Agent, or Firm* — Lerner, David, Littenberg, Krumholz & Mentlik, LLP

(57) ABSTRACT

A cylindrical column body (101) holds a filler. A pair of end caps (105, 106) covers both ends of the column body (101) and has a flow hole for a carrier liquid (111, 112) arranged in the center thereof. An end surface on the side of a large diameter portion (113*a*, 114*a*) of a pair of columnar joint members (113, 114) contacts an end surface of the pair of end caps (105, 106) and also has a communication hole (115, 116) arranged in the center thereof. A sealing member (117, 118) is arranged on a contact surface between the end cap (105, 106) and the joint member (113, 114). A bottomed cylindrical case (121) accommodates the pair of end caps (105, 106) and a large diameter portion of the pair of joint
(Continued)

members (113, 114) in an engaged state. A cover member (124) is detachably installed on a side of an opening of the case (121).

5 Claims, 3 Drawing Sheets

(52) U.S. Cl.
CPC ....... *G01N 30/6004* (2013.01); *G01N 30/606* (2013.01); *G01N 30/6047* (2013.01); *G01N 30/6052* (2013.01); *G01N 2030/8822* (2013.01)

(56) References Cited

FOREIGN PATENT DOCUMENTS

| | | |
|---|---|---|
| JP | H02-238362 A | 9/1990 |
| JP | H02-238363 A | 9/1990 |
| JP | H10-239297 A | 9/1998 |
| JP | H11-174036 A | 7/1999 |
| JP | 2001-249120 A | 9/2001 |
| JP | 2009-264859 A | 11/2009 |
| JP | 2012-202765 A | 10/2012 |
| WO | 03-046545 A1 | 6/2003 |
| WO | 2012-058513 A1 | 5/2012 |

OTHER PUBLICATIONS

Chinese Office Action for Application No. 201480026658.8 dated Jun. 13, 2016.
Extended European Search Report for EP 14765299, dated Oct. 5, 2016, 8 pages.

\* cited by examiner

COLUMN DEVICE FOR LIQUID CHROMATOGRAPHY AND LIQUID CHROMATOGRAPHY APPARATUS

CROSS-REFERENCE TO RELATED APPLICATION

The present application is a national phase entry under 35 U.S.C. §371 of International Application No. PCT/JP2014/056260, filed Mar. 11, 2014, which claims priority from JP Patent Application No. 2013-047880 filed Mar. 11, 2013, the disclosures of which are hereby incorporated by reference herein in their entirety.

TECHNICAL FIELD

The present invention relates to a column device for liquid chromatography and to a liquid chromatography apparatus using the same.

BACKGROUND ART

Liquid chromatography has been generally used for isolation, analysis, and separation of components of samples in fields such as organic chemistry, biochemistry, medicine, food science, and environmental science. There is a trend in the reduction in size of liquid chromatography apparatuses, and the capacity of their columns has been reduced.

As discussed in Patent Documents 1 and 2, column devices for liquid chromatography include a cylindrical column body which holds a column filler, and a pair of end caps which covers both ends of the column body, each end cap having a flow hole for the carrier liquid arranged in the center thereof, respectively. A pipe for introducing and delivering the carrier liquid is connected at an end on the side of an opening of the flow hole of the end cap.

REFERENCE DOCUMENT LIST

Patent Documents

Patent Document 1: Japanese Patent Application Laid-open Publication No. H11-174036
Patent Document 2: Japanese Patent Application Laid-open Publication No. 2001-249120

SUMMARY OF THE INVENTION

Problems to be Solved by the Invention

However, in the conventional column devices for liquid chromatography, an inlet-side pipe and an outlet-side pipe are screwed to be installed to each of a pair of end caps, and accordingly, when replacing the column device, it is necessary to unscrew at two locations including the joint for the inlet-side pipe and the joint for the outlet-side pipe. As described above, in the prior art, it has been required to perform a burdensome operation requiring much labor in the replacing of the column device.

In consideration of the above-described situation, the object of the present invention is to provide a column device for liquid chromatography of which a column device can be easily attached and detached by an operation performed at one location.

Means for Solving the Problems

In order to solve the above-described problem and achieve the above-described object, according to an aspect of the present invention, a column device for liquid chromatography includes a cylindrical column body which holds a column filler; a pair of end caps which covers the column body at both ends thereof, each end cap having a flow hole for a carrier liquid in the center thereof; a pair of columnar joint members including a large diameter portion arranged on one end thereof and a small diameter portion arranged on the other end thereof, in which an end surface on a side of the large diameter portion contacts end surfaces of the pair of end caps, each joint member having a communication hole which is arranged in the center of the joint member and agrees with the flow hole; a ring-like sealing member arranged so as to surround the flow hole and the communication hole between a contact surface between the end cap and the joint member; a bottomed cylindrical case which accommodates the pair of end caps and the large diameter portion of the pair of joint members in an engaged state; and a cover member detachably installed on a side of an opening of the case.

In this aspect of the present invention, a bottom of the case includes a through-hole which holds the large diameter portion of one joint member of the pair of the joint member and allows the small diameter portion thereof to go through. The cover member includes a through-hole which holds the large diameter portion of the other joint member of the pair of the joint member and allows the small diameter portion thereof to go through. The small diameter portion of the pair of joint member becomes a joint for a pipe constituting a flow path for the carrier liquid.

According to another aspect of the present invention, a liquid chromatography apparatus includes a sample injection device which injects a sample into a flow path for a carrier liquid; the column device having the above-described configuration, which is arranged in the flow path for the carrier liquid on a downstream side of the sample injection device and configured to separate components of the sample; and a detection device which is arranged on the flow path for the carrier liquid on a downstream side of the column device and configured to detect the separated components of the sample.

Effects of the Invention

In the present invention, the conventional end caps having a column body closing and sealing function and a pipe connection function is divided into end caps having the column body closing and sealing function and joint members having the pipe connection function, and these are brought into contact with one another via a sealing member, and a column body with the end caps and the joint members are accommodated and held in a bottomed cylindrical case and a cover member detachably installed on a side of an opening of the case.

With this configuration, the column body with the end caps can be exchanged (attached and detached) by performing an operation for attaching and detaching the cover member to and from the case. Accordingly, the attaching and detaching of the column body with the end caps can be readily performed, and thereby the convenience of the device can be increased. In addition, with the increased convenience, operation errors can be reduced, and thereby the risk of infection and the like can be avoided.

MODE FOR CARRYING OUT THE INVENTION

An embodiment of the present invention will be described in detail below.

Figure 1:
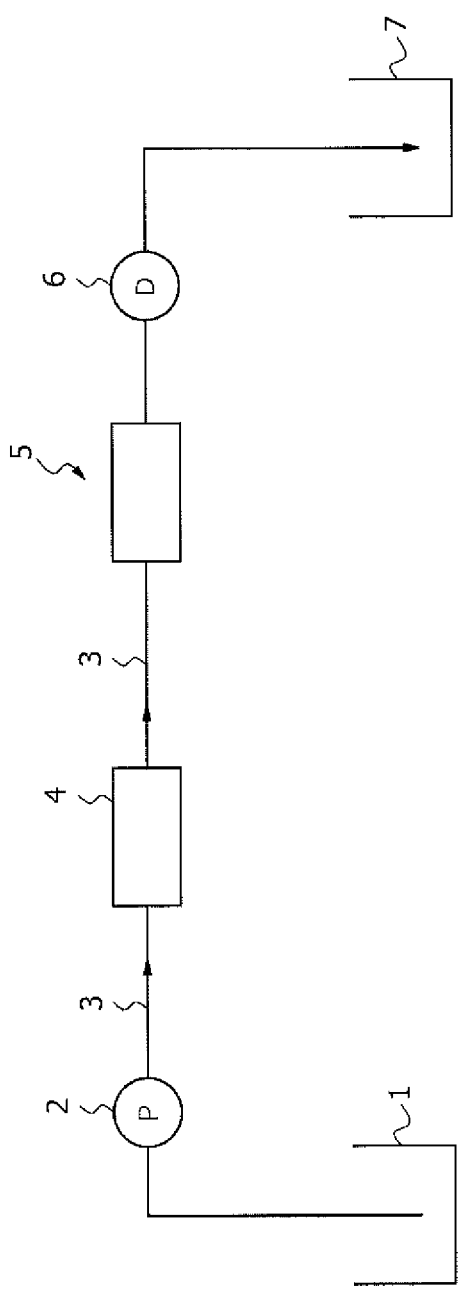
FIG. 1 is a schematic diagram which illustrates a liquid chromatography apparatus according to an embodiment of the present invention.

FIG. 1 is a schematic diagram which illustrates a liquid chromatography apparatus according to an embodiment of the present invention.

The chromatography apparatus illustrated in FIG. 1 is a flow type biochemical analysis apparatus that uses the principle of high-performance liquid chromatography (HPLC) and is used for analyzing hemoglobin components of blood such as hemoglobin A1c, for example.

The flow type biochemical analysis apparatus illustrated in FIG. 1 includes a reserve tank 1 for reserving a carrier liquid; a liquid feed pump 2 for continuously feeding the carrier liquid from the reserve tank 1; a flow path 3 for feeding the carrier liquid via the liquid feed pump 2; a sample injection device 4 for injecting a sample arranged in the carrier liquid flow path 3; a column device 5 for separating components of the sample arranged on a downstream side of the sample injection device 4; and a detection device 6 for detecting the separated components arranged on a downstream side of the column device 5.

The injection of the sample by the sample injection device 4 is performed by injecting the sample suctioned and sampled from a sample vessel (not illustrated) by using a needle (not illustrated) into the sample injection device 4. Detection signals from the detection device 6 are transmitted to a data processing device (not illustrated), and results of data processing by the data processing device are output as analysis results. The carrier liquid containing the analyzed sample is recovered into the waste liquid tank 7.

The column device 5 will be described in detail with reference to FIG. 2 (and FIG. 3).

Figure 2:
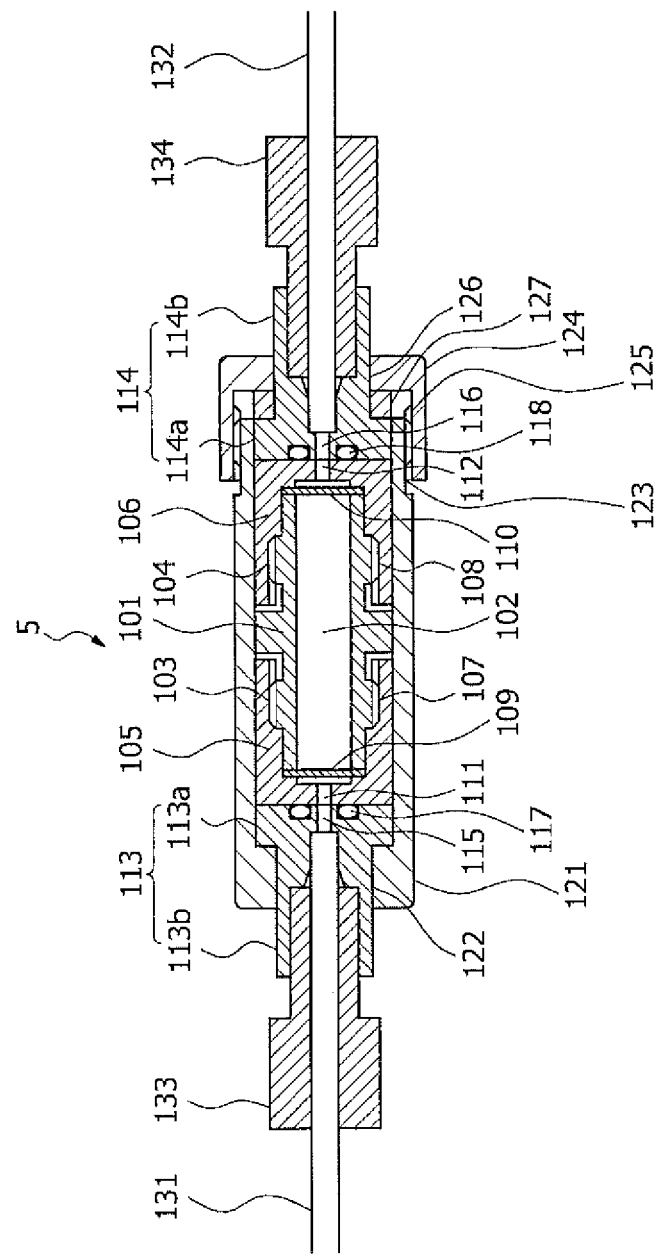
FIG. 2 is a cross section of a column device.
Figure 3:
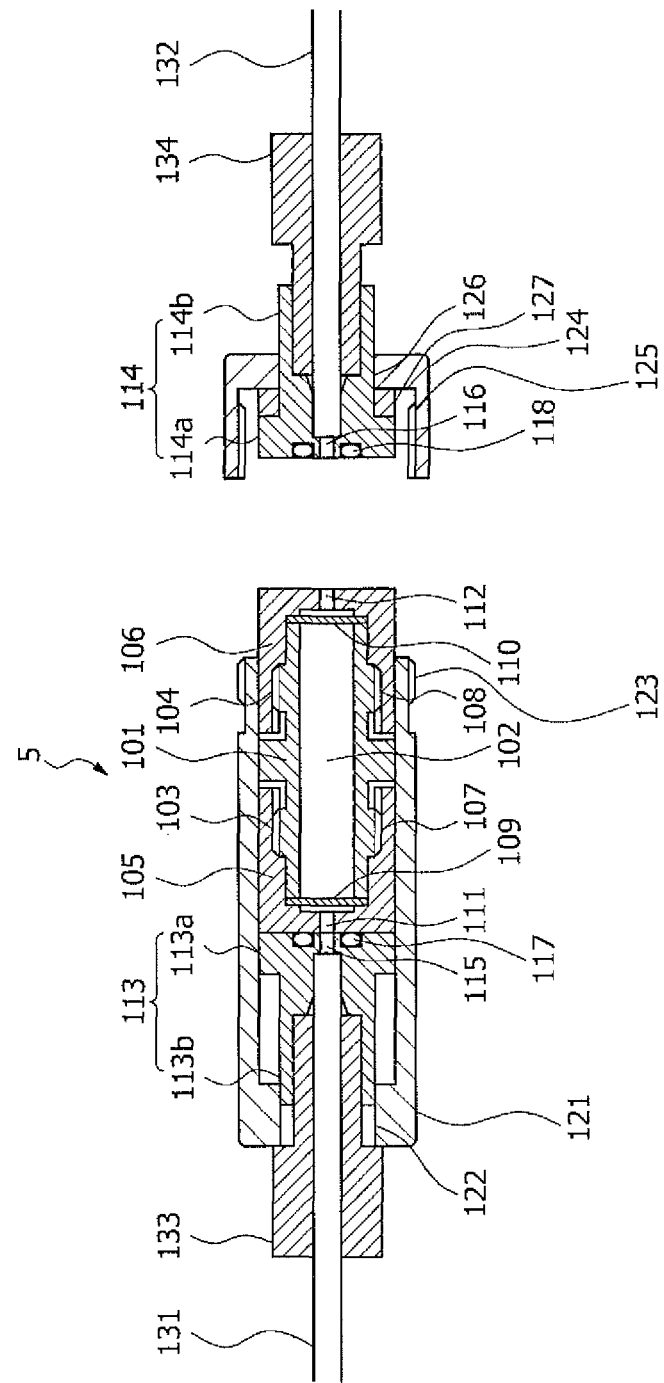
FIG. 3 is a cross section of the column device in a state in which it is replaced.

FIG. 2 is a cross section of the column device, and FIG. 3 is a cross section of the column device in a state in which it is exchanged.

A column body 101 is formed in a cylindrical shape, and a column filler 102 is held in the inside of the column body 101. Male screws 103, 104 are formed on an outer peripheral surface of the column body 101.

A pair of end caps 105, 106 is provided, which covers the column body 101 at both ends. Female screws 107, 108 are formed on an inner peripheral surface of the end caps 105, 106, which threadably engage with the male screws 103, 104 of the column body 101. As described above, the column body 101 and the end caps 105, 106 are fixed by using the above-described screws 103, 104, 107, and 108.

Filters 109, 110 are installed between both ends of the column body 101 and the end caps 105, 106.

A carrier liquid flow path 111, 112 is formed in the center of the end cap 105, 106.

A pair of joint members 113, 114 is arranged in correspondence with the pair of end caps 105, 106. The respective joint members 113, 114 have a columnar shape and include a large diameter portion 113a, 114a on one end and a small diameter portion 113b, 114b on the other end. An end surface on the side of the large diameter portion 113a, 114a contacts an end surface of the end caps 105, 106.

A communication hole 115, 116, which agrees with a flow hole 111, 112 on the side of the end caps 105, 106, is formed in the center of the joint member 113, 114.

A ring-like sealing member 117, 118 is arranged on a contact surface between the end cap 105, 106 and the joint member 113, 114 so as to surround the flow hole 111, 112 and the communication hole 115, 116. Specifically, a ring-like mount groove is formed on the contact surface on the side of the joint member 113, 114 and an O-ring or the like 117, 118 as the sealing member is installed into the mount groove.

In an inside of a bottomed cylindrical case 121, the column body 101, the pair of end caps 105, 106, and the large diameter portion 113a, 114a of the pair of joint members 113, 114 are accommodated in a mutually engaged state.

A through-hole 122 into which the small diameter portion 113b of the joint member 113 goes through is formed on the bottom of the case 121. The large diameter portion 113a of the joint member 113 is locked onto the bottom of the case 121, and the small diameter portion 113b is exposed to the outside from the through-hole 122.

A male screw 123 is formed on the outer peripheral surface on the side of the opening of the case 121.

A cover member 124 having a shape of a cap is formed so as to cover the opening of the case 121, and a female screw 125 is formed on the inner peripheral surface of the cover member 124. As described above, the case 121 and the cover member 124 are fixed by using the screws 123, 125. As the screws 123, 125, a double thread screw may be used.

Also on the cover member 124, a through-hole 126 through which the small diameter portion 114b of the joint member 114 goes is formed. The large diameter portion 114a of the joint member 114 is locked onto the bottom of the cover member 124, and the small diameter portion 114b is exposed to the outside from the through-hole 126.

The cover member 124 is fixed to the case 121, and thereby, the joint member 113, the end cap 105, the column body 101, the end cap 106, and the joint member 114 are held between the bottom of the case 121 and the back surface of the cover member 124. A spacer 127 is arranged between the joint member 114 and the cover member 124 where necessary.

A pipe connection hole is formed on the joint member 113, 114 to be connected to the communication hole 115, 116, and a carrier liquid pipe 131, 132 is connected to the pipe connection hole via a joint 133, 134.

In the column device 5 for liquid chromatography having the above-described configuration, in replacing the column body 101 with the end caps 105, 106, the cover member 124 is turned in relation to the case 121 to release the threadable engagement with the screw 123 and the screw 125. In releasing the engagement, by using a double thread screw for the screws 123, 125, the cover member 124 can be unscrewed by only slightly turning them.

Because the cover member 124 accompanies the joint member 114 that is connected to one pipe 132, the joint member 114, which is integrally arranged with the cover member 124, is separated from the end cap 106 when the cover member 124 is detached (see FIG. 3).

In this state, the joint member 113, the end cap 105, the column body 101, and the end cap 106 arranged in the inside of the case 121 are not locked.

Accordingly, by holding the other pipe 131 with a hand and pressing it into the case 121, the joint member 113 is pushed, thus the end cap 105, the column body 101, and the end cap 106 are pushed out at the same time, and as a result, at least the end cap 106 is exposed from the side of the opening of the case 121 (see FIG. 3).

It is thus possible to draw out the end cap 106, the column body 101, and the end cap 105 from the side of the opening the case 121 to replace the column body 101 with the end caps 105, 106.

In setting a new column body 101 with the end caps 105, 106, the column body 101 with the end caps 105, 106 is inserted into the case 121 and the end surface of the end cap 105 is abutted onto the end surface of the joint member 113 via the sealing member 117.

Then, the cover member 124 is screwed and installed on the side of the opening of the case 121 and the joint member 113, the end cap 105, the column body 101, the end cap 106, and the joint member 114 are held inside the bottom of the case 121 and the back surface of the cover member 124.

By performing this installation operation, the space between the joint member 113 and the end cap 105 and the space between the end cap 106 and the joint member 114 are sealed with the sealing member 117, 118, respectively.

As described above, the column body 101 with the end caps 105, 106 can be replaced only by assembling and disassembling the cover member 124.

According to the present embodiment, the joint member 113, 114 is provided with the mount groove for holding the ring-like sealing member 117, 118 arranged on the contact surface with the end cap 105, 106, i.e., in other words, the sealing member 117, 118 is held on the side of the joint member 113, 114 in this manner, and thereby the shape of the end cap 105, 106, which is a replaceable part, can be simplified.

In addition, according to the present embodiment, the cover member 124 has a shape of a cap and the female screw 125 that threadably engages the male screw 123 formed on the outer peripheral surface of the end on the opening of the case 121 is arranged on the inner peripheral surface of the cover member 124, and thereby the column body 101 with the end caps 105, 106 can be replaced by merely screwing and unscrewing the screws of the cover member 124.

Moreover, according to the present embodiment, double thread screws are used for the screws 123, 125 for assembling and disassembling the cover member 124, and thereby the cover member 124 can be attached and detached by only slightly turning the screws, and as a result, the operability can be improved. Examples of the material of the cover member 124 used in the present embodiment include metal materials, plastic resins, and the like, and by using ethylene tetrafluoroethylene (ETFE), which has a high friction coefficient, an effect of preventing loosened cover or the like can be increased while maintaining the operability at the same time.

In addition, according to the present embodiment, the spacer 127 is arranged between the cover member 124 and the joint member 114 that opposes the cover member 124, and thereby the cover member 124 and the joint member 114 can be opposed by adjusting the thickness of the spacer 127 even if the length of the column body 101 has varied, and thus the general-purpose properties can be increased. Further, the same part can be readily used for the pair of joint members 113, 114.

Because the spacer 127 is arranged and used in the present embodiment, not only can the general-purpose properties be increased, but also the effect of preventing a loosened cover can be increased by using fluoropolymer, silicone resin, fluororubber and the like as the material of the spacer 127 if the material of the cover member 124 is a material having a low friction coefficient similarly to the case in which a material having a high friction coefficient is used as the material of the cover member 124, for example.

Because the chromatography apparatus (flow type biochemical analysis apparatus) according to the present embodiment includes the sample injection device 4 for injecting a sample into the flow path 3 for a carrier liquid, the column device 5 having the above-described configuration arranged in the carrier liquid flow path on the downstream side of the sample injection device 4 to separate components of the sample, and the detection device 6 arranged in the flow path 3 for the carrier liquid on the downstream side of the column device 5 to detect the separated components of the sample, the column device 5 that is a consumable can be readily exchanged, and as a result, the operability of the device can be improved.

The embodiment illustrated in the Figures is a mere example of the present invention, and the present invention necessarily includes the example directly described by the above-described embodiment and also includes various modifications and alterations devised by one skilled in the art within the scope of the claims.

INDUSTRIAL APPLICABILITY

The column device for chromatography according to the present invention and the chromatography apparatus using the same are capable of isolating, analyzing, and separating components of various types of samples, and thus, have a great industrial applicability.

REFERENCE SYMBOL LIST

1 Reserve tank for carrier liquid
2 Liquid feed pump
3 Flow path for carrier liquid
4 Sample injection device
5 Column device
6 Detection device
7 Waste liquid tank
101 Column body
102 Column filler
103, 104 Male thread
105, 106 End cap
107, 108 Female thread
109, 110 Filter
111, 112 Flow hole
113, 114 Joint member
113a, 114a Large diameter portion
113b, 114b Small diameter portion
115, 116 Communication hole
117, 118 Sealing member (O-ring or the like)
121 Case
122 Through-hole
123 Male thread
124 Cover member
125 Female thread
126 Through-hole
127 Spacer
131, 132 Pipe for carrier liquid
133, 134 Joint

The invention claimed is:

1. A column device for liquid chromatography, comprising:
   a cylindrical column body that holds a column filler;
   a pair of end caps that cover the column body at both ends thereof, each end cap having a flow hole for a carrier liquid in the center thereof;
   a pair of columnar joint members, each joint member including a large diameter portion arranged on one end thereof and a small diameter portion arranged on the other end thereof, in which an end surface on a side of the large diameter portion contacts an end surface of the end cap, each joint member having a communication hole which is arranged in the center of the joint member and agrees with the flow hole;

a ring-like sealing member arranged so as to surround the flow hole and the communication hole between a contact surface between the end cap and the joint member;

a bottomed cylindrical case that accommodates the pair of end caps and the large diameter portion of the pair of joint members in an engaged state; and a cover member detachably installed on a side of an opening of the case, wherein a bottom of the case includes a through-hole that holds the large diameter portion of one joint member of the pair of the joint members and allows the small diameter portion thereof to go through, wherein the cover member includes a through-hole that holds the large diameter portion of the other joint member of the pair of the joint members and allows the small diameter portion thereof to go through, wherein the small diameter portion of the pair of joint members becomes a joint for a pipe constituting a flow path for the carrier liquid, wherein the end surface of the end cap is flat, and wherein the joint member includes a mount groove that is arranged on the contact surface between the end cap and the joint member, and holds the ring-like sealing member; and thereby the sealing member is held on the side of the joint member.

2. The column device for liquid chromatography according to claim 1, wherein the cover member has a cap-like shape and includes a female screw arranged on an inner peripheral surface thereof which threadably engages with a male screw formed on an outer peripheral surface of an end on a side of the opening of the case.

3. The column device for liquid chromatography according to claim 2, wherein the screws are a double thread screw.

4. The column device for liquid chromatography according to claim 1, wherein a spacer is arranged between the cover member and the joint member that opposes the cover member.

5. A liquid chromatography apparatus comprising:

a sample injection device that injects a sample into a flow path for a carrier liquid;

the column device according to claim 1 that is arranged in the flow path for the carrier liquid on a downstream side of the sample injection device and configured to separate components of the sample; and a detection device that is arranged on the flow path for the carrier liquid on a downstream side of the column device and configured to detect the separated components of the sample.

* * * * *